(12) United States Patent
Kennedy et al.

(10) Patent No.: US 10,442,871 B2
(45) Date of Patent: Oct. 15, 2019

(54) MODIFIED CYCLODEXTRINS FOR THE SELECTIVE SEQUESTRATION OF FENTANYL RELATED COMPOUNDS AND USES THEREOF

(71) Applicant: LAWRENCE LIVERMORE NATIONAL SECURITY, LLC, Livermore, CA (US)

(72) Inventors: Daniel Joseph Kennedy, Livermore, CA (US); Brian P. Mayer, Livermore, CA (US); Carlos A. Valdez, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 15/630,869

(22) Filed: Jun. 22, 2017

(65) Prior Publication Data

US 2018/0371110 A1  Dec. 27, 2018

(51) Int. Cl.

| A61K 31/724 | (2006.01) |
| C08B 37/16 | (2006.01) |
| C07D 309/10 | (2006.01) |
| C07D 221/00 | (2006.01) |
| C07D 211/28 | (2006.01) |

(52) U.S. Cl.
CPC ........ *C08B 37/0012* (2013.01); *A61K 31/724* (2013.01); *C07D 211/28* (2013.01); *C07D 221/00* (2013.01); *C07D 309/10* (2013.01)

(58) Field of Classification Search
CPC .......................... C08B 37/0012; A61K 31/724
See application file for complete search history.

(56) References Cited

U.S. PATENT DOCUMENTS

| 6,670,340 B1 | 12/2003 | Zhang et al. | |
| RE44,733 E * | 1/2014 | Zhang | 514/231.5 |
| 9,120,876 B2 | 9/2015 | Davuluri et al. | |

OTHER PUBLICATIONS

Abramowitz, A. "Elementary Analytical Methods. In Handbook of Mathematical Functions: with Formulas, Graphs, and Mathematical Tables", Dover Publications, Inc., New York, NY, 1965.
Adam J. M. et al., "Cyclodextrin-Derived Host Molecules as Reversal Agents for the Neuromuscular Blocker. Rocuronium Bromide: Synthesis and Structure-Activity Relationships", Journal of Medicinal Chemistry, 2002, 45, 1806-1816.
Baer, H. H. et al., "Improved preparation of hexakis(6-deoxy)cyclomaltohexaose and heptakis(6-deoxy)cyclomaltoheptaose", Elsevier Science Publishers B.V., 1992, Amsterdam.
Berendsen, H. J. C. et al., "Molecular-Dynamics with Coupling to an External Bath", J. Chem. Phys. 81, 1984, 3684-90.
Case, D. A. et al., "The Amber Biomolecular Simulation Programs", J. Comput. Chem. 26, 2005, 1668-88.
Cézard, C. et al., "Molecular Dynamics Studies of Native and Substituted Cyclodextrins in Different Media: 1. Charge Derivation and Force Field Performances", Phys. Chem. Chem. Phys. 13, 2011, 15103-21.
Cooper, A. et al., "Mutual Induced Fit in Cyclodextrin-Rocuronium Complexes", Org. Biomol. Chem. 3, 2005, 1863-1971.
Cameron, K. S. et al., "An NMR Study of Cyclodextrin Complexes of the Steroidal Neuromuscular Blocker Drug Rocuronium Bromide", Magn. Reson. Chem. 40, 2002, 251-260.
Cameron, K. S. et al., "NMR Diffusion Coefficient Study of Steroid-Cyclodextrin Inclusion Complexes", Magn. Reson. Chem. 40, 2002, S106-S109.
Højsted, J. et al., "Addiction to Opioids in Chronic Pain Patients: a Literature Review", Eur. J. Pain, 11, 2007, 490-518.
Darden, T. et al., "Particle mesh Ewald: An N log(N) Method for Ewald Sums in Large Systems", J. Chem. Phys. 98, 1993, 10089-92.
Jakalian, A. et al., "Dfficient Generation of High-Quality Atomic Charges. AM1-BCC Model: I. Method", J. Comput. Chem. 21, 2000, 132-46.
Jorgensen, W. L. et al., "Comparison of simple potential functions for simulating liquid water", J. Chem. Phys. 79, 1983, 926.
Kollman, P. A. et al., "Calculating Structures and Free Energies of Complex Molecules: Combining Molecular Mechanics and Continuum Models", Acc. Chem. Res. 33, 2000, 889-97.
Mayer, B. P. et al., "Solution-State Structure and Affinities of Cyclodextrin: Fentanyl Complexes by Nuclear Magnetic Resonance Spectroscopy and Molecular Dynamics Simulation", J. Phys. Chem. B, 120, 2016, 2423-33.
Miller, B. R. III. Et al., "An Efficient Program for End-State Free Energy Calculations", J. Chem. Theory Comput. 8, 2012, 3314-21.
Onufriev, A. et al., "Exploring Protein Native States and Large-Scale Conformational Changes with a Modified Generalized Born Model", Proteins: Struc., Func., Bioinf. 55, 2004, 383-94.
Peng, P. W. H. et al., "A Review of the Use of Fentanyl Analgesia in the Management of Acute Pain in Adults", Anesthesiology, 90, 1999, 576-599.
Pettersen, E.F. et al., "UCSF Chimera—a Visualization System for Exploratory Research and Analysis", J. Comput. Chem. 25, 1977, 1605-12.
Ryckaert, J.P. et al., "Numerical Integration of the Cartesian Equations of Motion of a System with Constrains: Molecular Dynamics of n-Alkanes", J. Comput. Phys.23, 1977, 327-341.
Sehgal, N. et al., "Prescription Opioid Abuse in Chronic Pain: a Review of Opioid Abuse Predictors and Strategies to Curb Opioid Abuse", Pain Physician, 15, 2012, ES67—ES92.

(Continued)

*Primary Examiner* — Leigh C Maier
(74) *Attorney, Agent, or Firm* — Perkins Coie, LLP

(57) ABSTRACT

Novel thioalkylcarboxylate-modified CDs and pharmaceutical compositions comprising these thioalkylcarboxylate-modified CDs are disclosed, as well as methods of using the disclosed thioalkylcarboxylate-modified CDs and pharmaceutical compositions thereof to neutralize or reduce undesired effects or symptoms associated with one or more fentanyl related compounds in a subject in need thereof. The use of the disclosed thioalkylcarboxylate-modified CDs to detect the presence of one or more fentanyl related compounds in a sample is also disclosed, which comprises contacting the sample with said thioalkylcarboxylate-modified CDs or a composition comprising these CDs.

5 Claims, 5 Drawing Sheets
(4 of 5 Drawing Sheet(s) Filed in Color)

(56) References Cited

OTHER PUBLICATIONS

Shalley, C. A. et al., "Analytical Methods in Supramolecular Chemistry, Second, Completely Revised and Enlarged Edition", Wiley-VCH, Weinheim, 2011, pp. 27-66.
Thordarson, P. et al., "Determining Association Constants from Titration Experiments in Supramolecular Chemistry", Chem. Soc. Rev. 40, 2011, 1305-23.
Wang, J. et al., "Development and Testing of a General Amber Force Field", J. Comput. Chem. 25, 2004, 1157-74.

\* cited by examiner

MODIFIED CYCLODEXTRINS FOR THE SELECTIVE SEQUESTRATION OF FENTANYL RELATED COMPOUNDS AND USES THEREOF

BACKGROUND OF THE INVENTION

Fentanyl, N-(1-phenylethylpiperidin-4-yl)-N-phenylpropanamide, is a synthetic μ-opioid receptor agonist. Fentanyl in its free base form has the chemical structure:

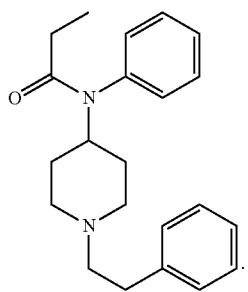 [SMILES: CCC(=O)N(c1ccccc1)C1CCN(CCc2ccccc2)CC1]

Originally designed as an anesthetic, fentanyl has become an important tool for managing breakout pain in a clinical setting, with a potency roughly 100 times that of morphine (Peng and Sandler 1999). Fentanyl related compounds may produce stronger euphoric effects, which gives rise to a significant potential for misuse (Højsted and Sjøgren 2007; Sehgal and Smith 2012). Thus there is a need for chemical countermeasures (i.e., "antidotes") to neutralize fentanyl related compounds' environmental and physiological threats.

BRIEF DESCRIPTION OF DRAWINGS

This application contains at least one drawing executed in color. Copies of this application with color drawing(s) will be provided by the Office upon request and payment of the necessary fees.

FIG. 3a: Fentanyl (carbon atoms in cyan) aligned "down" with amide half near primary rim of suβ−0 (carbon atoms in green).

FIG. 3b: Fentanyl (carbon atoms in cyan) aligned "up" with amide half near primary rim of suβ−0 (carbon atoms in green).

FIG. 3c: Binding energies for three carboxylate subetadex complexes (with suβ−1, suβ−0, and suβ+1).

DETAILED DESCRIPTION

Overview

Figure 1:
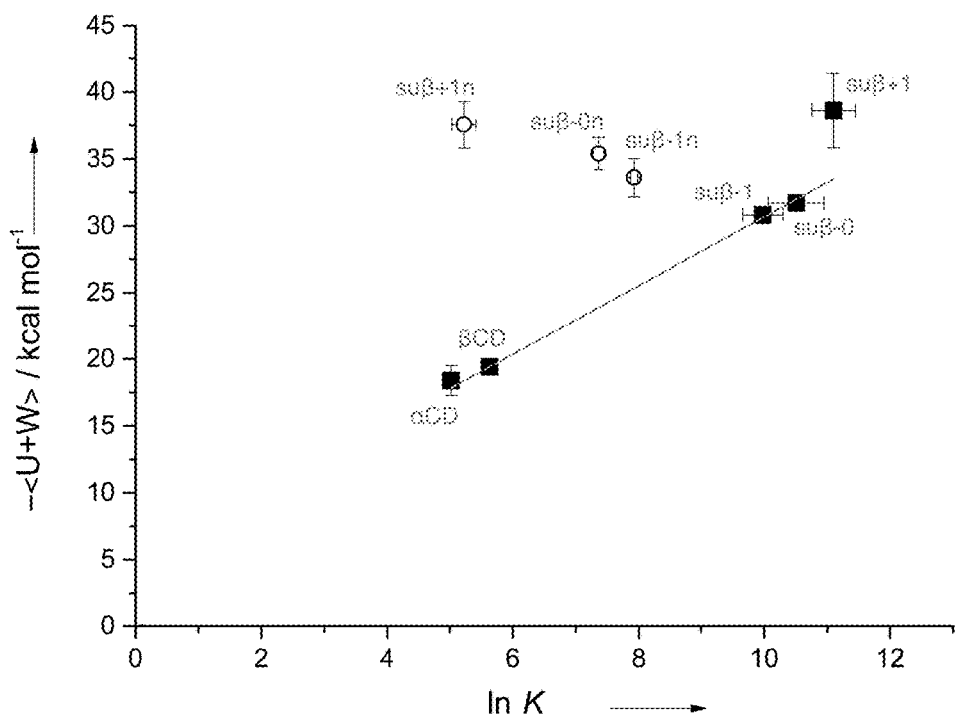
FIG. 1: NMR binding affinities versus enthalpic energies determined from simulation for the dominant conformer of fentanyl bound to thioether modified βCDs (suβ−1n, suβ−0n, suβ−+1n, suβ−1, suβ−0, and suβ+1), and unmodified αCD and βCD.

Cyclodextrins (CDs) are cyclic oligosaccharides composed of glucopyranosyl units connected through α-1,4-glycosidic linkages. CDs resemble a truncated cone open at both ends, and have been used as water-soluble host molecules capable of binding guest molecules within their hydrophobic cavity. Typical CDs contain a number of glucose monomers ranging from six to eight units. CDs containing six, seven and eight glucose units are often referred to as alpha-CDs (α-CDs or αCDs), beta-CDs (βCDs or β-CDs), and gamma-CDs (γCDs or γ-CDs), respectively.

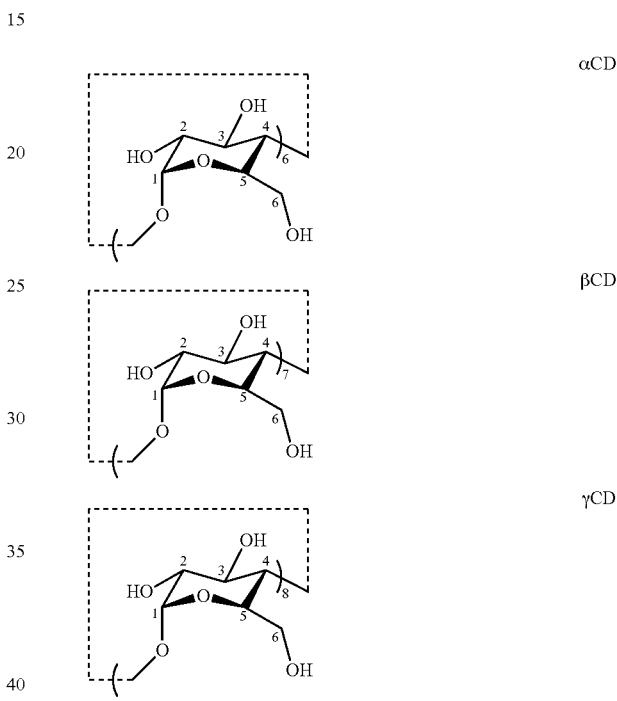

A modified γ-CD, sugammadex (Suγdex), has been used to sequester the neuromuscular blocking agent rocuronium with a reported binding constant on the order of $10^4$-$10^5$ $M^{-1}$, a degree of binding affinity approaching those observed for highly specific enzyme:ligand systems (Cameron et al. 2002, Cameron and Fielding 2002, Cooper et al. 2005). However, no previously identified CDs have shown significant affinity to a fentanyl related compound.

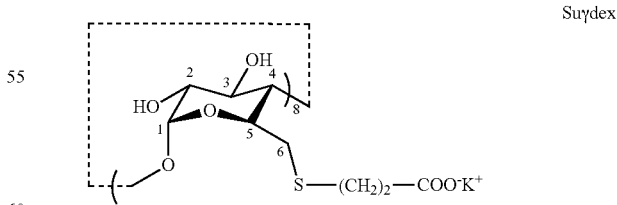

As set forth herein, a set of thioalkylcarboxylate-modified CDs was identified with unexpectedly high binding affinity to one or more fentanyl related compounds. The binding constant (K) of these thioalkylcarboxylate-modified CDs to one or more of the fentanyl compounds is on the order of $10^2$ to $10^4$ $M^{-1}$. Based on this high binding affinity, the thioalkylcarboxylate-modified CDs disclosed herein may be used as neutralizers, sequestration entities, or antidotes for one or more fentanyl related compounds, and may also be used in detecting one or more of the fentanyl compounds in a sample.

Accordingly, provided herein are novel thioalkylcarboxylate-modified CDs and pharmaceutical compositions comprising these thioalkylcarboxylate-modified CDs, as well as methods of using the disclosed thioalkylcarboxylate-modified CDs and pharmaceutical compositions thereof to neutralize or reduce undesired effects or symptoms associated with one or more fentanyl related compounds in a subject in need thereof. Also provided herein is the use of the disclosed thioalkylcarboxylate-modified CDs to detect the presence of one or more fentanyl related compounds in a sample by contacting the sample with said thioalkylcarboxylate-modified CDs or a composition comprising these CDs.

Definitions

The term "neutralizing" as used herein with regard to an effect or symptom (e.g., an effect or symptom associated with a fentanyl related compound) means reducing or stopping the effect or symptom.

The term "pharmaceutically acceptable carrier" as used herein refers to a carrier that does not cause an allergic reaction or other untoward effect in patients to whom it is administered and is compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

The term "subject" as used herein refers to a mammal, including a human. In certain embodiments, a subject has been exposed, is currently being exposed, or is at risk of being exposed to one or more fentanyl related compounds.

As used herein, a "fentanyl related compound" is a μ-opioid receptor agonist compound having the structure set forth in Formula II:

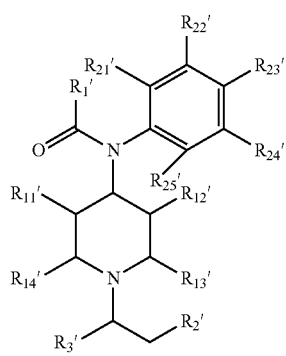

Formula II including salts and solvates thereof, and stereoisomers thereof, wherein:

$R_1'$ is selected from the group consisting of optionally substituted $C_1$-$C_6$ alkyl, optionally substituted $C_1$-$C_6$ alkenyl, optionally substituted furanyl, optionally substituted $C_1$-$C_6$ carboxylester, and optionally substituted $C_1$-$C_6$ alkoxyl;

$R_2'$ is selected from the group consisting of optionally substituted phenyl, optionally substituted thiophenyl, optionally substituted furanyl, optionally substituted carboxyester and optionally substituted tetrazolone;

$R_3'$ is selected from the group consisting of H, optionally substituted $C_1$-$C_6$ alkyl and hydroxyl;

$R_{11}'$-$R_{14}'$ are independently selected from the group consisting of H, optionally substituted $C_1$-$C_6$ alkyl, optionally substituted $C_2$-$C_6$ alkenyl, optionally substituted $C_1$-$C_6$ alkoxyl, and optionally substituted phenyl; and $R_{21}'$-$R_{25}'$ are independently selected from the group consisting of H, optionally substituted $C_1$-$C_6$ alkyl and halogen (e.g., F, Cl, Br, and I). In certain embodiments, a fentanyl related compound may exhibit μ-opioid receptor agonist activity that is the same as, greater than, or less than that of fentanyl.

Unless otherwise specified, "optionally substituted" means optionally substituted with one or more substitution groups selected from the group consisting of $C_1$-$C_6$ alkyl, hydroxyl, oxo, and halogen (e.g., F, Cl, Br, and I).

In certain embodiments, examples of the salts of a fentanyl related compound include, without limitation, acid additive salts such as hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts.

The singular form "a," "an," and "the" include plural references unless the context clearly dictates otherwise. For example, the term "a pharmaceutically acceptable carrier" includes a plurality of pharmaceutically acceptable carriers, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely exemplary and that equivalents of such are known in the art.

Thioether Modified CDs

As set forth in the example section below, a library of unmodified and modified CDs were evaluated for binding to one or more fentanyl related compounds. Among the unmodified α-, β-, and γ-CDs, γ-CDs had the lowest binding affinity to fentanyl related compounds, while β-CD exhibited the highest binding affinity (Table 2). Modified β-CD with a hydroxypropyl substitution at C2 position of the glucose units (2HP-βCD) or an amino substitution at the C6 position of the glucose units (6-deoxy-6-amino-β-CD) exhibited decreased binding affinity to fentanyl related compounds versus the unmodified β-CD. However, a set of thioether modified β-CDs were unexpectedly found to exhibit higher binding affinities for one or more fentanyl related compounds than the corresponding unmodified β-CD. A set of β-CDs modified with anionic thioether showed higher binding affinities than Sugammadex (Table 3). The binding affinity and binding energy of the modified anionic βCDs increased as the size of the modification group increased (FIG. 1).

Accordingly, provided herein in certain embodiments are thioether modified CDs that bind one or more fentanyl related compounds. In certain embodiments, these thioether modified CDs bind one or more fentanyl related compounds with a higher degree of binding affinity than the corresponding unmodified CD. For example, in certain embodiments, a thioether modified β-CDs provided herein binds one or more fentanyl related compounds with a K at least about 1.4 times, 8 times, 10 times, 13.5 times, 15 times, 50 times, 100 times, 150 times, 300 times, 335 times, 350 times, or 500 times that of the corresponding unmodified β-CD. In certain embodiments, the thioether modified CDs provided herein bind one or more fentanyl related compounds via non-covalent interactions.

In certain embodiments, the thioether modified β-CDs provided herein have the structure set forth in Formula I:

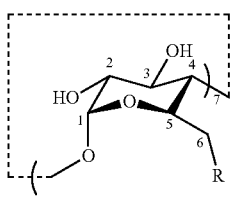

Formula I including salts thereof and pharmaceutically acceptable salts thereof, wherein:
R is —S—$(CH_2)_n$—C(=O)$OR_0$, —S—$(CH_2)_{n+1}$—$OR_0$ or —S—$(CH_2)_n$—C(=O)$O^-M^+$;
$R_0$ is H;
M is selected from the group consisting of Li, Na, K, $NH_4$, $Ca_{1/2}$, and $Mg_{1/2}$; and
n is 0, 1, 2, 3, 4, 5, 6, 7, 8, 9, or 10.

In certain embodiments of the thioether modified β-CDs having the structure of Formula I, when R is —S—$(CH_2)_{n+1}$—OH, n is not 2.

Also disclosed herein are thioether modified CDs having the structure set forth in Formula III:

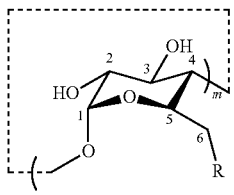

Formula III including salts thereof and pharmaceutically acceptable salts thereof, wherein:
R is defined the same as in Formula I; and
m is 6, 7, or 8.

In certain embodiments of the thioether modified CDs having the structure of Formula III, when m is 8, R is not —S—$(CH_2)_2$—COOH or —S—$(CH_2)_2$—$COO^-M^+$, The thioether modified CDs disclosed herein may be identified by a chemical name as shown in Table 1 based on the definition of m, R, and n, respectively. Thioether modified CDs of Formula III wherein R is —S—$(CH_2)_n$—C(=O)$O^-M^+$) are also referred to herein as the anionic thioether modified CDs. The "N" or "n" in the alternative chemical names means neutral for thioether modified CDs with R being —S—$(CH_2)_{n+1}$—OH. The "0," "+1," "−1," and "+2" refer to the differences between n and 2. Provided herein in certain embodiments are the thioether modified β-CDs set forth in Table 1, as well as salts and pharmaceutically acceptable salts thereof.

TABLE 1

Alternative chemical names of thioether modified CDs (Formula III)

| Compound No. | Alternative Chemical Name | m | R | n |
|---|---|---|---|---|
| 4 | Suαdex or Suα | 6 | —S—$(CH_2)_n$—C(=O)$O^-K^+$ | 2 |
| N/A | Suβdex + 2 or Suβ + 2 | 7 | | 4 |
| 9 | Suβdex + 1 or Suβ + 1 | | | 3 |
| 7 | Suβdex or Suβ − 0 | | | 2 |
| 5 | Suβdex − 1 or Suβ − 1 | | | 1 |
| 11 | Suγdex or Suγ | 8 | | 2 |
| N/A | SuβN + 2 or Suβ + 2n | 6 | —S—$(CH_2)_{n+1}$—OH | 4 |
| 10 | SuβN + 1 or Suβ + 1n | | | 3 |
| 8 | SuβN or Suβ − 0n | | | 2 |
| 6 | SuβN − 1 or Suβ − 1n | | | 1 |

In certain embodiments, salts, including pharmaceutically acceptable salts, of the disclosed compounds include, without limitation, one or more salts selected from the group consisting of ammonium salts, lithium salts, sodium salts, potassium salts, calcium salts, and magnesium salts.

Compositions/Pharmaceutical Compositions

Provided herein in certain embodiments are compositions comprising, consisting of, or consisting essentially of one or more of the thioether modified CDs disclosed herein. In certain embodiments, these compositions further comprise one or more carriers.

In certain embodiments, the compositions provided herein comprise one or more thioether modified CDs having a structure set forth in Formula I or III. In certain embodiments, the compositions comprise a thioether modified β-CDs listed in Table 1.

In certain embodiments, the compositions provided herein are pharmaceutical compositions comprising one or more pharmaceutically acceptable carriers. In certain embodiments, these pharmaceutical compositions comprise a therapeutically effective of a thioether modified CD provided herein, including for example an amount effective for neutralizing or reducing an undesired effect or symptom of one or more fentanyl related compounds in a subject.

Neutralizing Fentanyl Related Compounds

In certain embodiments, binding of a thioether modified CD provided herein to one or more fentanyl related compounds results in complete or partial deactivation of the one or more fentanyl related compounds. Accordingly, provided herein in certain embodiments are methods of fully or partially neutralizing one or more fentanyl related compounds using one or more of the thioether modified CDs provided herein. In certain of these embodiments, one or more fentanyl related compounds is neutralized in a subject in need thereof. These methods comprise administering to the subject a therapeutically effective amount of one or more thioether modified CDs provided herein. In certain embodiments, the thioether modified CDs have a structure set forth in Formula I or III. In certain embodiments, the thioether modified CDs are thioether modified β-CDs listed in Table 1.

In certain embodiments, the thioether modified CD is administered to a subject as part of a pharmaceutical composition provided herein.

A therapeutically effective amount of a thioether modified CD for neutralizing one or more fentanyl related compounds is an amount that partially or completely eliminates one or more activities of one or more fentanyl related compounds (e.g., μ-opioid receptor agonist activity). In certain embodiments, the therapeutically effective amount is about 0.5 to about 2.0, about 0.8 to about 1.5, about 0.9 to about 1.2, or about 1.0 times the molar amount of a fentanyl related compound that the subject has been exposed to or is expected to be exposed to.

Reducing Undesired Effects or Symptoms Associated with Fentanyl Related Compounds Provided herein are methods of reducing undesired effects or symptoms associated with fentanyl related compounds thereof in a subject in need thereof comprising administering to the subject a therapeutically effective amount of one or more of the thioether modified CDs provided herein. In certain embodiments, the thioether modified CDs have a structure set forth in Formula I or III. In certain embodiments, the thioether modified CDs are thioether modified β-CDs listed in Table 1.

In certain embodiments, the thioether modified CD is administered to a subject as part of a pharmaceutical composition provided herein.

In certain embodiments, reduction of effects or symptoms results in complete cessation or prevention of said effects or symptoms. In other embodiments, the effects or symptoms may still be present, but to a lesser degree than that observed prior to administration of thioether modified CDs.

A therapeutically effective amount of a thioether modified CD as disclosed herein for preventing undesired effects or symptoms associated with a fentanyl related compound is an amount that reduces said effects or symptoms to at least a minimum desired degree, e.g., by 10%, 20%, 30%, 40%, 50%, 60%, 70%, 80%, 90%, 95%, 98%, 99%, or 99.5%. In certain embodiments, a therapeutically effective amount of a thioether modified CD results in complete prevention or cessation of the effect or symptom. In certain embodiments, the therapeutically effective amount of the thioether modified CD is about 0.5 to about 2.0, about 0.8 to about 1.5, about 0.9 to about 1.2, or about 1.0 times of the molar amount of the one or more fentanyl related compounds to which the subject may be exposed.

Administration Routes

The thioether modified CDs and compositions thereof disclosed herein may be administered via any pathway known in the art, including but not limited to topical administration, oral administration, intradermal administration, intramuscular administration, intraperitoneal administration, intravenous administration, intravesical infusion, subcutaneous administration, transdermal administration, and transmucosal administration. The choice of a particular route of administration depends on the formulation of the drug and is within the purview of one of ordinary skill in the art.

Methods of Detecting a Fentanyl Related Compound

Provided herein in certain embodiments are methods of detecting a fentanyl related compound in a sample comprising applying to the sample an effective amount of one or more thioether modified CDs provided herein. Fluorescence-based or UV-based detection technologies for one or more fentanyl related compounds can be generated using these thioalkylcarboxylate modified CDs. For example, one can envision the initial trapping or complex formation between one of the CDs with a given fluorescent or UV-active compound (e.g. dye) resulting in a measurable change of the luminescent properties of this compound once inside the CD cavity. Following this initial event, incubation of the complex with a given fentanyl would result in the expulsion of the fluorescent or UV-active compound from the interior of the CD cavity and this event would be followed by a marked change in the luminescent properties of the compound. The process would be driven by the higher affinity of the fentanyl for the thioether modified CD over the fluorescent or UV-active compound.

Preparation of Thioether Modified CDs

Provided herein in certain embodiments are methods for preparing a thioether modified CD disclosed herein. In certain embodiments, methods are provided for preparing a thioalkylcarboxylate modified CD of Formula III or a salt thereof comprising a coupling step comprising reacting a thiol R'—H and a CD derivative having the structure of Formula IV to provide a coupling β-CD product having the structure of Formula V:

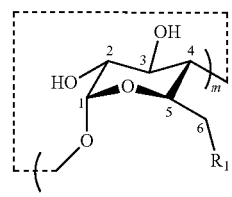

Formula IV

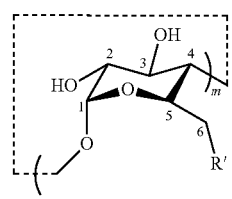

Formula V wherein:
R is the same as defined in Formula I;
R' is R or a derivative thereof when $R_0$ is H in R;
m is 6, 7, or 8; and
$R_1$ is halogen, e.g., Cl, Br, or I.

In certain embodiments, $R_0$ is H, and a derivative of R comprises R with the hydroxyl group and/or carboxylic group protected. For example, the hydroxyl group may be protected by an ether or ester group; and the carboxylic group can be protected by an ester or amide group. The preparation method optionally further comprises a deprotecting step to unmask the protected carboxylic group of the R' group in the coupling β-CD product (Formula IV).

The following examples are provided to better illustrate the claimed invention and are not to be interpreted as limiting the scope of the invention. To the extent that specific materials are mentioned, it is merely for purposes of illustration and is not intended to limit the invention.

One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Materials and Methods
Reagents

Reagents and solvents were purchased from commercial sources and were used as received. Methyl 3-mercaptopropionate (98%), cesium carbonate (99%) and 2-mercapto-1-ethanol were purchased from Alfa Aesar (Ward Hill, Mass.). Methyl thioglycolate was purchased from Pfaltz and Bauer, Inc. (Waterbury, Conn.). Methyl 4-sulfanylbutanoate was purchased from Enamine Ltd. (Kyiv, Ukraine). N-methyl-2-pyrrolidone was purchased from Applied Biosystems, Thermo Fisher (Grand Island, N.Y.). 4-mercapto-1-butanol and 3-mercapto-1-propanol were purchased from Aldrich Co. (St. Louis, Mo.). Deuterated water (D2O) was purchased from Cambridge Isotope Laboratories, Inc. (Tewksbury, Mass.).

Methods

Centrifugation was performed in a Eppendorf centrifuge model 5810R at 3220 rpm for 5 minutes, using Falcon tubes (50 mL) purchased from VWR (Aurora, Colo.). Solvents were removed using an IKA RV8 model rotary evaporator coupled to a KNF-Lab vacuum filtration pump and a VWR RS-232 cooling/circulating system (9° C. water/ethylene glycol 1:1).

NMR Methods $^1$H NMR (600 MHz), $^{13}$C NMR (150 MHz) and $^{13}$C-DEPT NMR (150 MHz) spectra were recorded in $D_2O$ and the chemical shifts were referenced to an acetonitrile internal standard set at 2.0144 ppm unless otherwise specified. Spectra were obtained using a Bruker Avance III 600 MHz instrument equipped with a Bruker TCI 5 mm cryoprobe (Bruker Biospin, Billerica, Mass.) at 30.0±0.1° C. One-dimensional 1H NMR data were collected with water suppression by excitation sculpting with gradients. For each 1-D experiment, 16 to 128 transients (using 4 dummy scans, depending on the analyte concentration) were collected into 65536 data points using a 4.0 s acquisition time and a 1.0 s relaxation delay. Prior to the Fourier transformation the free induction decays (FIDs) were apodized with an exponential decay equivalent to 0.25 Hz line broadening. Two-dimensional ROESY spectra were acquired using 16384 data points with 1024 increments, 8 to 32 scans for each increment, and a continuous wave spin lock with a 200 ms mixing time and a frequency of 3.57 kHz. A weak CW field was chosen to minimize potential TOCSY-type contributions to the ROESY spectrum. Phase-sensitive data was collected using a 3-9-19 water suppression scheme 18 aided with pulsed field gradients over a 5.4 kHz spectral window.

NMR data is reported as follows: chemical shift (δ) (parts per million, ppm); multiplicity: s (singlet), d (doublet), t (triplet), dd (doublet of doublets), td (triplet of doublets), m (multiplet), app (apparent) and br (broad); coupling constants (J) are given in Hertz (Hz).

Data Analysis and Error Estimation

All data, particularly nonlinear regression of titration curves, were analyzed with the aid of Mathematica 8.0 software (Wolfram Research, Champaign, Ill.). ROESY data were used to inform the peaks chosen to extract data on binding strength. Selected peaks from so-called "reporter protons" were monitored and all data were fit simultaneously by minimizing the sum-squared errors of all peak data. In this manner, an average binding constant was obtained that included contributions from dynamics, motional degrees of freedom, and the effects of binding thereon for each of the reporter protons as discussed below. To minimize excessive handling of the potentially dangerous fentanyl, traditional measurement error was not determined by performing three or more replicates of each host:guest pair. Instead, error was estimated using 95% confidence limits for K values extracted from each of the reporter protons' data separately. A small experiment demonstrated that errors determined using individual uncertainties from NLLS results were comparable to those derived through multiple replicates.

Molecular Dynamics (MD) Simulations

Figure 3A:
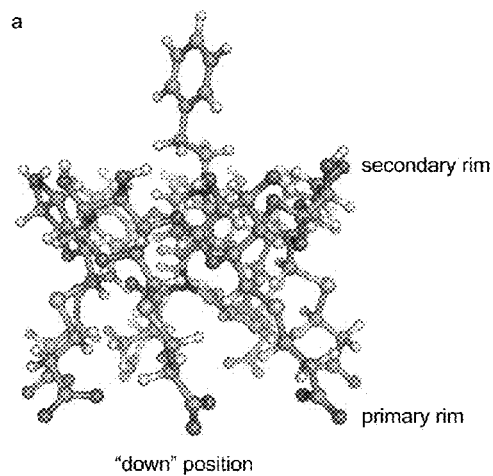
FIGS. 3a-3c: Molecular dynamics (MD results for the host:guest complex with two orientations.
Figure 3B:
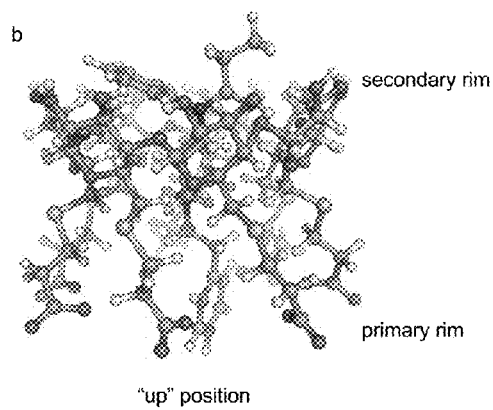

MD were performed with AMBER (version 12) (Case et al. 2005) using the recent charges and parameters of Cezard et al. for the cyclodextrins (Cezard et al. 2011) and the GAFF force field for the various fentanyls (Wang et al. 2004). Fentanyl charges were generated by AM1-BCC calculations (Jakalian et al. 2000) in the program ANTECHAMBER (Wang et al. 2004). The program CHIMERA was used to model the fentanyl:CD complexation processes (Pettersen et al. 2004). The CD and CD:fentanyl complexes were solvated in a box of TIP3P water sufficient in size to have at least 15 Å of water between the solute and the solvent interface (~51×51×51 Å3 initial box size) (Jorgensen et al. 1983). To neutralize the systems, sufficient sodium ions (typically one) were added to the system. The systems consisted of about 12 500 atoms (~4100 water molecules). Each system was energy minimized using 250 steps of steepest descent and 1500 steps of conjugate gradient. Constant temperature and pressure dynamics (NPT) were performed on these minimized systems (Miller et al. 2012; Berendsen et al. 1984). Coupling constants of 0.2 and 0.22 ps were used for temperature and pressure, respectively. Periodic boundary conditions were used and electrostatic interactions were treated by particle mesh Ewald methods with a 9 Å cutoff in direct space and a 1 Å grid (Darden et al. 1993). Bonds containing hydrogen were constrained using SHAKE (Ryckaert et al. 1977), and a time step of 2 fs was used in each simulation. The systems were initially coupled to a heat bath at 100 K for the first 100 ps, then increased to 200 K for the next 100 ps, and finally raised to 300 K for the remainder of the simulation. Each simulation was performed for a total of 10 or 30 ns depending on the CD guest. Initial simulations involved only single trajectories (no replicates), but it was universally observed that the βCD structure did not change significantly during dynamics, and that the root mean squared deviation of the non-hydrogen atoms relative to the average structure quickly plateaued by 1 ns. The first 2.5 ns of the 300 K dynamics were used for equilibration. To obtain more comprehensive data and statistical information, ten replicate simulations (10 ns each) were performed by four complexes between all four charged fentanyls and βCD where the guest molecule was parallel to the wider CD rim (see FIGS. 3a-3c). These replicate simulations were characterized by changing the seed value for generating the initial velocities for the system. The free energy of binding between the cyclodextrins and fentanyls were estimated using the molecular mechanics generalized Born surface area (MM-GBSA) method from snapshots of the solvated trajectories (Kollman et al. 2000). MM-GBSA energy calculations were performed on replicate simulations and then averaged to obtain the average binding energy for a particular fentanyl:CD system. The binding free energy was estimated by the equation:

$$\Delta G_{binding} = G_{complex} - (G_{cyclodextrin} + G_{fentanyl})$$

where each term, G is estimated as the sum of gas-phase molecular mechanics energy $E_{gas}$ and the solvation energy Gsol:

$$G_{total} = E_{gas} + G_{sol} \quad 5$$

The contribution of entropy was neglected in these free energy calculations. The solvation free energy ($G_{sol}$) is the sum of the polar and nonpolar solvation energies of the molecules determined by solving the generalized Born (GB) equation. The binding free energies for the complexes were calculated using the MMPBSA.py script in AMBER12 on snapshots from each 7.5 ns trajectory (Miller et al. 2012). The modified Onufriev-Bashford-Case-I GB (ib=2) model was used for the calculation with a fentanyl salt concentration of 0.24 mM (Onufriev et al. 2004). The surface tension used to calculate the nonpolar contribution to the free energy of solvation was 0.0072 kcal mol$^{-1}$ Å$^{-2}$.

Formalism for "Multi-Conformation" (E.g., Two-State) Binding Model

Establishing an analytical formalism for a two-state binding system began with expressions for the equilibrium binding constants and host/guest mass balances (Thordarson 2011).

$$K_u = \frac{[HG_u]}{[H][G_u]} \quad K_d = \frac{[HG_d]}{[H][G_d]}$$

$$[H]_0 = [H] + [HG_u] + [HG_d]$$

$$[G_u]_0 = [G_u] + [HG_u] \quad [G_d]_0 = [G_d] + [HG_d]$$

$$[G]_0 = [G_u]_0 + [G_d]_0$$

$$[G_u]_0 = [G_d]_0$$

Two expressions for K were required, one for each fentanyl configuration: u="up" and d="down." [H] was the concentration of free host. [G$_u$] and [G$_d$] were the concentrations of free guest in the up and down configurations, respectively. [HG$_u$] and [HG$_d$] were the concentrations of the up and down fentanyl:CD complexes, respectively. These concentrations were invoked for the completeness of the model. The subscript "0" referred to the initial total concentration of a particular species. The last equality reflected that the up and down states were equally likely due to isotropic tumbling of fentanyl in solution. Using these equations, a cubic polynomial was obtained in terms of free host [H], the roots of which were found as described below.

Solving for Cubic Roots

The roots of cubic equations were solved based on work and information presented previously (Abramowitz 1965) (Cubic formula http://mathworld.wolfram.com/CubicFormula.html). For the Tschirnhaus-Vieta approach, all three cubic roots were real if f<0 (as given below). Physically relevant/realizable values for K$_{11}$ and K$_{21}$ were only possible for this numerical fitting algorithm if this condition was satisfied for the entire range of experimental [G]$_0$ and [H]$_0$ values.

The treatment below was strictly for 1:1 binding equilibria where the compound that bound could adopt one of two orientations (that cannot be distinguished between when free in solution).

In physical variable space:

$$a[H]^3 + b[H]^2 + c[H] + d = 0$$

$$a = K_u K_d$$

$$b = (K_u + K_d) + K_u K_d ([G]_0 - [H]_0)$$

$$c = 1 + (K_u + K_d)([G]_0 - [H]_0)$$

$$d = -[H]_0$$

Variable Transformation:

$$f = \frac{1}{3}\left(\frac{3c}{a} - \frac{b^2}{a^2}\right)$$

$$g = \frac{1}{27}\left(\frac{2b^3}{a^3} - \frac{9bc}{a^2} + \frac{27d}{a}\right)$$

$$h = \frac{g^2}{4} + \frac{f^3}{27}$$

$$i = \sqrt{\frac{g^2}{4} - h}$$

$$j = \sqrt[3]{i}$$

$$k = \arccos\left(\frac{-g}{2i}\right)$$

$$L = -j$$

$$M = \cos\left(\frac{k}{3}\right)$$

$$N = \sqrt{3}\,\sin\left(\frac{k}{3}\right)$$

$$P = \frac{-b}{3a}$$

Arriving at final cubic roots:

$$[H] = \max_i \chi_i$$

Physically relevant solution was the maximum root:

$$\chi_1 = 2j\cos\left(\frac{k}{3}\right) + P$$

$$\chi_2 = L(M + N) + P$$

$$\chi_3 = L(M - N) + P$$

Example 1: Synthesis of CD Derivatives

The thioether modified CDs were synthesized using C6-per-brominated CDs in the presence of cesium carbonate in dry N-methyl-2-pyrrolidinone (NMP).

1.1: Synthesis of Per-Brominated CDs

Hexakis-(1), heptakis-(2) and octakis (3)-C6-brominated CDs employed in this work were synthesized using the in situ formation of the Vilsmeier-Haack reagent, e.g., as described by Baer et al.[1] Thus, as a general procedure for the synthesis of these per-brominated CDs, triphenylphosphine (123 mmol) was dissolved in anhydrous NMP (100 mL) in a 500 mL round-bottomed flask equipped with a stir bar and the solution cooled to ~4° C. using an ice bath. Bromine (123 mmol) was added dropwise to the stirring solution and the mixture was allowed to warm to ambient temperature over 30 minutes. To the above mixture, the corresponding CD (7.7 mmol) was added in small portions. Once all the CD was added, the mixture was heated to 80°

C. and maintained at this temperature overnight. The following day, NMP was removed from the flask on a rotavap at 90° C. to provide a yellow, thick oily residue. NaOMe/MeOH solution (150 mL, 3M) with triethylamine (10 mL) was added into the oil residue and after stirring for 10 minutes at ambient temperature. A beige solid was precipitated from the mixture after adding cooled, iced water (400 mL), and isolated by filtration. The resulted filtrate was further crystallized at 4° C. overnight to provide an off-white crystal. Both the beige solid and off-white crystal were determined to be the per-brominated CD. Yields for the α-, β- and γ-CD were 33%, 39% and 32%, respectively (Baer et al. 1992).

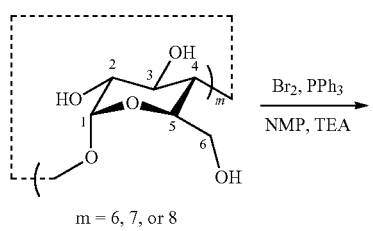

m = 6, 7, or 8

Synthesis of C6-Per-Brominated CDs (α, β, and γ)

1.2: Synthesis of Anionic Thioether Modified CDs, e.g., Suαdex (4), Suβdex-1 (5), Suβdex (7), Suβdex+(9), Suγdex (11)

Anhydrous cesium carbonate was added to a per-brominated CD (in dry NMP) at ambient temperature with vigorous stirring. To the mixture, the thiol-containing ester (e.g., a methyl ester) was added via syringe and the resulting mixture was heated to 55° C. overnight. The following day, the mixture was cooled to ambient temperature and added dropwise using a glass pipette to a stirring acetone solution. The white flakes that precipitated were collected using a centrifuge and washed with acetone to remove NMP. The modified CD (as the methyl ester) was in pure form (>98% by $^1$H NMR in DMSO-$_{d6}$) and was taken directly onto the next step without further purification. The per-methylester CD was treated with an aqueous solution of KOH with stirring. The resulting suspension became a solution upon stirring for over 10 minutes and then allowed to stir at this temperature overnight. The following day, the mixture was precipitated as above, using acetone to obtain the anionic CDs in pure form after several rounds of centrifugation with intermediary acetone washes.

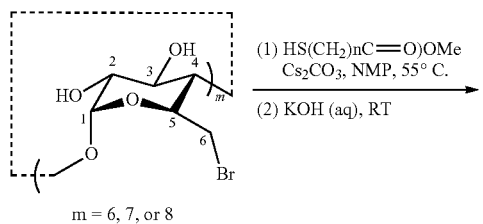

m = 6, 7, or 8

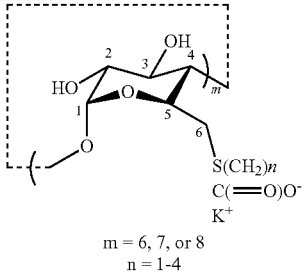

m = 6, 7, or 8
n = 1-4

Synthesis of anionic thioether modified CDs (α, β, and γ)

Preparation of Suadex (4)

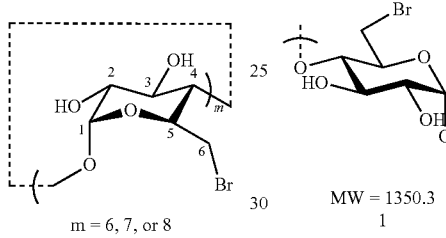

MW = 1350.3
1

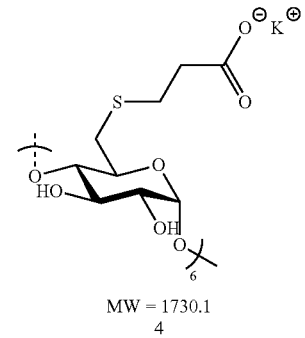

MW = 1730.1
4

Hexakis-6-bromo-6-deoxy-β-cyclodextrin 1 (1.6 g, 1.18 mmol) was made into a suspension in N-methyl-2-pyrrolidone (NMP, 20 mL) in a 100 mL round bottomed flask equipped with a stir bar. Upon gentle heating the cyclodextrin fully dissolved forming a light tan-colored solution. To this solution, cesium carbonate (3.84 g, 11.8 mmol, 10 equiv. to cyclodextrin) was added in small portions followed by the addition via syringe of methyl 3-mercaptopropionate (1.3 mL, 1.42 g, 11.8 mmol, 10 equiv. to cyclodextrin). The resulting mixture was heated to 55° C. overnight with vigorous stirring. The following day, the suspension was cooled to ambient temperature and the mixture added dropwise to a vigorously stirring 500 mL Erlenmeyer flask filled with 300 mL of acetone to induce precipitation of the modified cyclodextrin. Stirring of the suspension was done at ambient temperature for 10 minutes and the fine, white precipitate was collected first by centrifugation. The white solid was then washed with deionized water (2×50 mL) and centrifuged again. It was found that two washings followed by centrifugation were sufficient to remove all the residual cesium carbonate and NMP. The collected precipitate was taken up in acetone (50 mL) and vacuum filtered through a fritted disc filter (medium porosity) and dried under vacuum for 30 minutes to furnish the methyl ester cyclodextrin intermediate as a pure off-white solid (1.65 g, 88%). Methyl ester β-cyclodextrin intermediate (1.65 g, 1.04 mmol) was treated with 1 M KOH/H$_2$O (7.8 mL, 7.8 mmol, 7.5 equiv. to cyclodextrin) in a 20 mL scintillation vial equipped with a stir bar. The initial suspension became a full solution (light tan in color) after 10 minutes of stirring at ambient temperature. The mixture was vigorously stirred overnight. The light tan solution was added dropwise to a stirring acetone bath (300 mL) in a 500 mL Erlenmeyer flask. White flakes precipitated out upon the addition of the mixture and these were collected by centrifugation. Additionally, the white solid was re-suspended, washed with MeOH (2×50 mL) and collected by centrifugation. The additional methanol wash was found to efficiently remove any remaining KOH. Lastly, the solid was vacuum filtered, washed with MeOH (2×20 mL) and dried under vacuum for 2 h. The procedure yielded pure Suβdex (4) potassium salts (1.49 g, 83%). $^1$H NMR (D$_2$O, 600 MHz) δ 5.04 (s, 6H), 3.99 (br s, 6H), 3.89 (t, J=7.8, 6H), 3.57-3.53 (m, 12H), 3.11 (d, J=13.2, 6H), 2.92 (dd, J=13.2, 6.6, 6H), 2.80 (t, J=7.8, 12H), 2.43 (td, J=7.8, 12H); $^{13}$C NMR (D$_2$O, 150 MHz) δ 180.6, 100.7 (br), 83.1 (br), 73.2, 71.9, 71.3, 37.7, 33.5, 29.4; LC-MS (TOF): [M−2H]$^{2−}$, m/z 749.1440 (749.1450 calc.)

Preparation of Suβdex-1 (5)

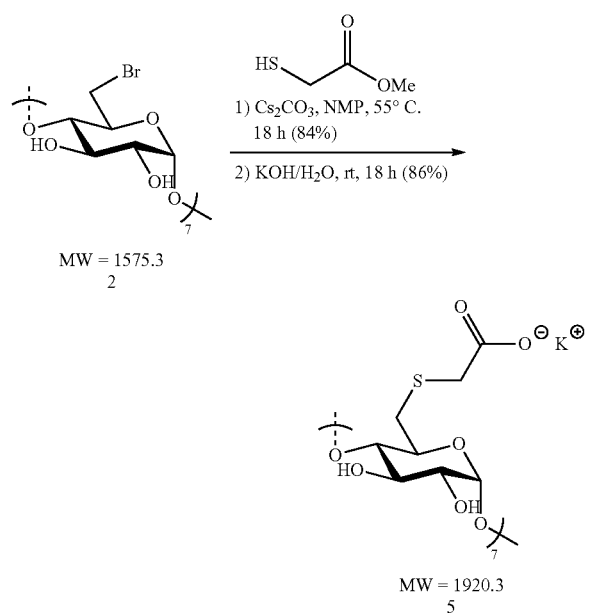

Heptakis-6-bromo-6-deoxy-β-cyclodextrin 2 (1.2 g, 0.76 mmol) was made into a suspension in N-methyl-2-pyrrolidone (NMP, 20 mL) in a 100 mL round bottomed flask equipped with a stir bar. To this solution, cesium carbonate (2.48 g, 7.6 mmol, 10 equiv. to cyclodextrin) was added in small portions followed by the addition via syringe of methyl thioglycolate (0.68 mL, 0.81 g, 7.6 mmol, 10 equiv. to cyclodextrin). The resulting mixture was heated to 55° C. overnight with vigorous stirring. The following day, the suspension was cooled to ambient temperature and the mixture added dropwise to a vigorously stirring 500 mL Erlenmeyer flask filled with 300 mL of acetone to induce precipitation of the modified cyclodextrin. Stirring of the suspension was done at ambient temperature for 10 minutes and the white precipitate was collected first by centrifugation. The white solid was then washed with deionized water (2×50 mL) and centrifuged again. The collected precipitate was taken up in acetone (50 mL) and vacuum filtered through a fritted disc filter (medium porosity) and dried under vacuum for 30 minutes to furnish the methyl ester β-cyclodextrin intermediate as a pure, off-white solid (1.1 g, 84%). The methyl ester β-cyclodextrin intermediate (1.1 g, 0.63 mmol) was treated with 1 M KOH/H$_2$O (4.73 mL, 4.73 mmol, 7.5 equiv. to cyclodextrin) in a 20 mL scintillation vial equipped with a stir bar. The initial suspension became a full solution (light tan in color) after 10 minutes of stirring at ambient temperature. The mixture was vigorously stirred overnight. The light tan solution was added dropwise to a stirring acetone bath (300 mL) in a 500 mL Erlenmeyer flask. White flakes precipitated out upon the addition of the mixture and these were collected by centrifugation. Additionally, the white solid was re-suspended, washed with MeOH (2×50 mL) and collected by centrifugation. Again, it was found that the additional methanol wash was found to efficiently remove any remaining KOH in the mixture. Lastly, the solid was vacuum filtered, washed with MeOH (2×20 mL) and dried under vacuum for 2 h. The procedure yielded pure Suβdex-1 (5) potassium salt (1.04 g, 86%). $^1$H NMR (D$_2$O, 600 MHz) δ 5.09 (s, 6H), 4.05 (t, J=7.2, 6H), 3.92 (t, J=9.6, 6H), 3.68-3.62 (m, 12H), 3.43-3.36 (m, 12H), 3.16 (d, J=14.4, 6H), 2.97 (app dd, J=14.4, 6.6, 6H); $^{13}$C NMR (D$_2$O, 150 MHz) δ 177.6, 101.8, 83.6, 73.0, 72.4, 71.5, 38.6, 33.7; LC-MS (TOF): [M−2H]$^{2−}$, m/z 825.1158 (825.1157 calc.)

Preparation of Suβdex (7)

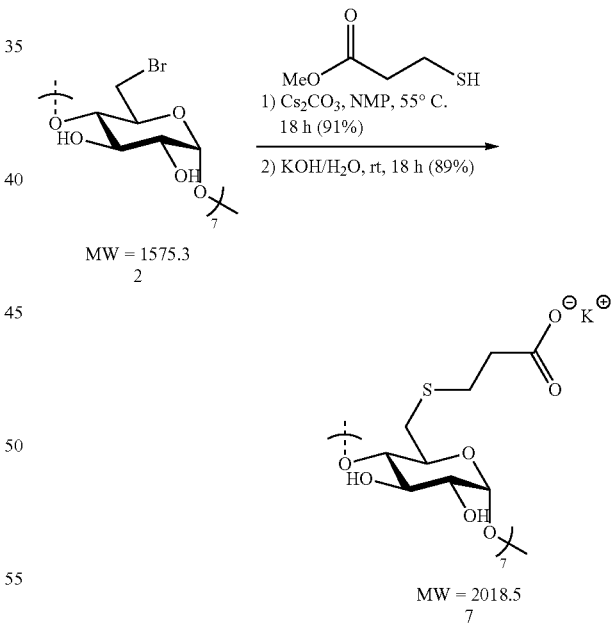

Heptakis-6-bromo-6-deoxy-β-cyclodextrin 2 (1.5 g, 0.95 mmol) was made into a suspension in N-methyl-2-pyrrolidone (NMP, 20 mL) in a 100 mL round bottomed flask equipped with a stir bar. Upon gentle heating the cyclodextrin fully dissolved forming a light tan-colored solution. To this solution, cesium carbonate (3.1 g, 9.5 mmol, 10 equiv. to cyclodextrin) was added in small portions followed by the addition via syringe of methyl 3-mercaptopropionate (1.04 mL, 1.14 g, 9.5 mmol, 10 equiv. to cyclodextrin). The resulting mixture was heated to 55° C. overnight with vigorous stirring. The following day, the suspension was cooled to ambient temperature and the mixture added dropwise to a vigorously stirring 500 mL Erlenmeyer flask filled with 300 mL of acetone to induce precipitation of the modified cyclodextrin. Stirring of the suspension was done at ambient temperature for 10 minutes and the fine, white precipitate was collected first by centrifugation. The white solid was then washed with deionized water (2×50 mL) and centrifuged again. The collected precipitate was taken up in acetone (50 mL) and vacuum filtered through a fritted disc filter (medium porosity) and dried under vacuum for 30 minutes to furnish the methyl ester cyclodextrin intermediate as a pure off-white solid (1.6 g, 91%). Thus, methyl ester β-cyclodextrin intermediate (1.6 g, 0.86 mmol) was treated with 1 M KOH/H$_2$O (6.45 mL, 6.45 mmol, 7.5 equiv. to cyclodextrin) in a 20 mL scintillation vial equipped with a stir bar. The initial suspension became a full solution (light tan in color) after 10 minutes of stirring at ambient temperature. The mixture was vigorously stirred overnight. The light tan solution was added dropwise to a stirring acetone bath (300 mL) in a 500 mL Erlenmeyer flask. White flakes precipitated out upon the addition of the mixture and these were collected by centrifugation. Additionally, the white solid was re-suspended, washed with MeOH (2×50 mL) and collected by centrifugation. Lastly, the solid was vacuum filtered, washed with MeOH (2×20 mL) and dried under vacuum for 2 h. The procedure yielded pure Suβdex (7) potassium salt (1.55 g, 89%). $^1$H NMR (D$_2$O, 600 MHz) δ 5.05 (d, J=3.0, 6H), 3.94 (td, J=9.0, 1.8, 6H), 3.84 (t, J=9.6, 6H), 3.56-3.53 (m, 12H), 3.09 (d, J=12.0, 6H), 2.93 (dd, J=13.8, 7.2, 6H), 2.80 (t, J=7.2, 12H), 2.43 (td, J=7.2, 3.6, 12H); $^{13}$C NMR (D$_2$O, 150 MHz) δ 180.6, 101.4, 83.3, 73.0, 72.4, 72.4, 37.7, 33.4, 29.6; LC-MS (TOF): [M−2H]$^{2-}$, m/z 874.1705 (874.1635 calc.)

Preparation of Suβdex+1 (9)

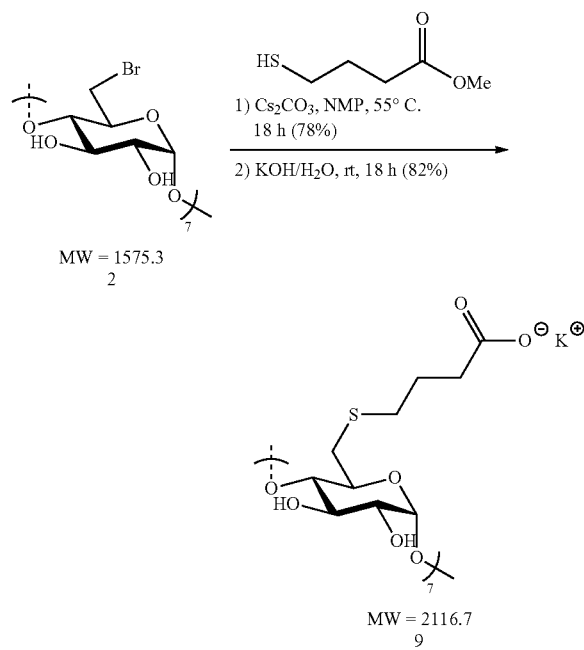

Heptakis-6-bromo-6-deoxy-β-cyclodextrin 2 (1.0 g, 0.63 mmol) was made into a suspension in N-methyl-2-pyrrolidone (NMP, 20 mL) in a 100 mL round bottomed flask equipped with a stir bar. Upon gentle heating the cyclodextrin fully dissolved forming a light tan-colored solution. To this solution, cesium carbonate (2.1 g, 6.3 mmol, 10 equiv. to cyclodextrin) was added in small portions followed by the addition via syringe of methyl 4-sulfanylbutanoate (0.84 g, 6.3 mmol, 10 equiv. to cyclodextrin). The resulting mixture was heated to 55° C. overnight with vigorous stirring. The following day, the suspension was cooled to ambient temperature and the mixture added dropwise to a vigorously stirring 500 mL Erlenmeyer flask filled with 300 mL of acetone to induce precipitation of the modified cyclodextrin. Stirring of the suspension was done at ambient temperature for 10 minutes and the fine, white precipitate was collected first by centrifugation. The white solid was then washed with deionized water (2×50 mL) and centrifuged again. The collected precipitate was taken up in acetone (50 mL) and vacuum filtered through a fritted disc filter (medium porosity) and dried under vacuum for 30 minutes to furnish the methyl ester β-cyclodextrin intermediate as a pure, off-white solid (1.07 g, 87%). Thus, methyl ester β-cyclodextrin intermediate (1.07 g, 0.55 mmol) was treated with 1 M KOH/H$_2$O (4.13 mL, 4.13 mmol, 7.5 equiv. to cyclodextrin) in a 20 mL scintillation vial equipped with a stir bar. The initial suspension became a full solution (light tan in color) after 10 minutes of stirring at ambient temperature. The mixture was vigorously stirred overnight. The light tan solution was added dropwise to a stirring acetone bath (300 mL) in a 500 mL Erlenmeyer flask. White flakes precipitated out upon the addition of the mixture and these were collected by centrifugation. Additionally, the white solid was re-suspended, washed with MeOH (2×50 mL) and collected by centrifugation. Lastly, the solid was vacuum filtered, washed with MeOH (2×20 mL) and dried under vacuum for 2 h. The procedure yielded pure Suβdex+1 (9) potassium salts (0.95 g, 82%). $^1$H NMR (D$_2$O, 600 MHz) δ 5.12 (d, J=3.0, 6H), 3.94 (t, J=9.0, 6H), 3.89 (t, J=9.6, 6H), 3.57-3.52 (m, 12H), 3.10 (d, J=13.2, 6H), 2.92 (dd, J=13.2, 7.8, 6H), 2.67-2.59 (m, 12H), 2.22 (t, J=7.2, 12H), 2.16 (br s, 6H), 1.84-1.77 (m, 12H); $^{13}$C NMR (D$_2$O, 150 MHz) δ 182.3, 100.0, 82.2, 72.8, 71.9, 71.3, 36.7, 33.4, 32.7, 26.2; LC-MS (TOF): [M−2H]$^{2-}$, m/z 923.2228 (923.2253 calc.)

Preparation of Suγdex (11)

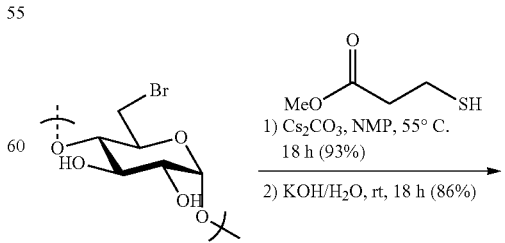

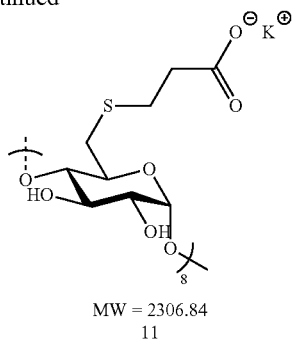

MW = 2306.84
11

Octakis-6-bromo-6-deoxy-β-cyclodextrin 3 (1.6 g, 0.89 mmol) was made into a suspension in N-methyl-2-pyrrolidone (NMP, 20 mL) in a 100 mL round bottomed flask equipped with a stir bar. Upon gentle heating the cyclodextrin fully dissolved forming a light tan-colored solution. To this solution, cesium carbonate (2.9 g, 8.9 mmol, 10 equiv. to cyclodextrin) was added in small portions followed by the addition via syringe of methyl 3-mercaptopropionate (0.99 mL, 1.07 g, 8.9 mmol, 10 equiv. to cyclodextrin). The resulting mixture was heated to 55° C. overnight with vigorous stirring. The following day, the suspension was cooled to ambient temperature and the mixture added dropwise to a vigorously stirring 500 mL Erlenmeyer flask filled with 300 mL of acetone to induce precipitation of the modified cyclodextrin. Stirring of the suspension was done at ambient temperature for 10 minutes and the fine, white precipitate was collected first by centrifugation. The white solid was then washed with deionized water (2×50 mL) and centrifuged again. The collected precipitate was taken up in acetone (50 mL) and vacuum filtered through a fritted disc filter (medium porosity) and dried under vacuum for 30 minutes to furnish the methyl ester β-cyclodextrin intermediate as a pure off-white solid (1.75 g, 93%). Thus, methyl ester β-cyclodextrin intermediate (1.75 g, 0.83 mmol) was treated with 1 M KOH/H$_2$O (6.3 mL, 6.3 mmol, 7.5 equiv. to cyclodextrin) in a 20 mL scintillation vial equipped with a stir bar. The initial suspension became a full solution (light tan in color) after 10 minutes of stirring at ambient temperature. The mixture was vigorously stirred overnight. The light tan solution was added dropwise to a stirring acetone bath (300 mL) in a 500 mL Erlenmeyer flask. White flakes precipitated out upon the addition of the mixture and these were collected by centrifugation. Additionally, the white solid was washed with MeOH (2×50 mL) and collected by centrifugation. Lastly, the solid was vacuum filtered, washed with MeOH (2×20 mL) and dried under vacuum for 2 h. The procedure yielded pure Suβdex (11) potassium salts (1.65 g, 86%). $^1$H NMR (D$_2$O, 600 MHz) δ 5.12 (s, 6H), 4.00 (br s, 6H), 3.89 (d, J=9.2, 6H), 3.60-3.57 (m, 12H), 3.07 (d, J=14.2, 12H), 2.95 (dd, J=14.2, 5.9, 6H), 2.80 (t, J=7.1, 12H), 2.45-2.42 (m, 12H); $^{13}$C NMR (D$_2$O, 150 MHz) δ 180.6, 101.0, 82.3, 72.6, 72.3, 71.2, 37.7, 33.4, 29.6; LC-MS (TOF): [M−2H]$^{2-}$, m/z 999.1925 (999.1961 calc.)

1.3. Synthesis of Neutral Thioether Modified CDs, e.g., SuβN−1 (6), SuβN (8), and SuβN+1 (10)

Anhydrous cesium carbonate was added to a per-brominated CD (in dry NMP) at ambient temperature with vigorous stirring. To the mixture, the thiol-containing ester (e.g., a methyl ester) was added via syringe and the resulting mixture was heated to 55° C. overnight. The following day, the mixture was cooled to ambient temperature and added dropwise using a glass pipette to a stirring acetone solution. The white flakes that precipitated were collected using a centrifuge and washed with acetone to remove NMP. Further washing of the flakes with deionized water, heating, crystallization, and centrifugation provided the neutral thioether modified CD in pure form (>95% by $^1$H NMR).

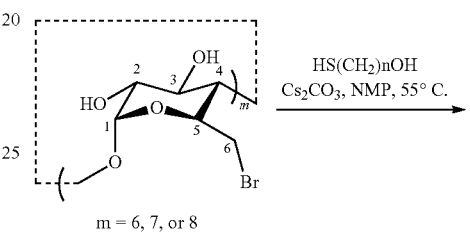

m = 6, 7, or 8

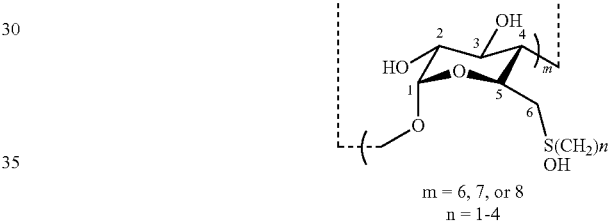

m = 6, 7, or 8
n = 1-4

Synthesis of Neutral Thioether Modified CDs (α, β, and γ)

Preparation of SuβN−1 (6)

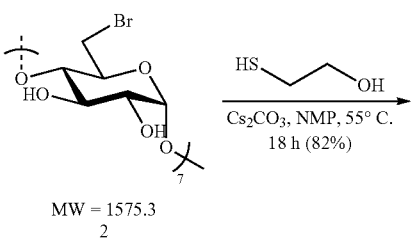

MW = 1575.3
2

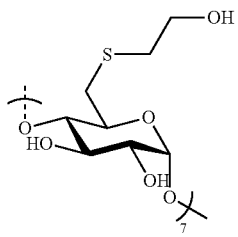

MW = 1555.8
6

Heptakis-6-deoxy-6-bromo-β-cyclodextrin 2 (1.2 g, 0.76 mmol) was made into a suspension with N-methyl-2-pyrrolidone (NMP, 20 mL) in a 100 mL round bottomed flask equipped with a stir bar. Upon gentle heating the cyclodextrin fully dissolved forming a light tan-colored solution. To this solution, cesium carbonate (2.48 g, 7.6 mmol, 10 equiv. to cyclodextrin) was added in small portions followed by the addition via syringe of 2-mercaptoethanol (0.53 mL, 0.59 g, 7.6 mmol, 10 equiv. to cyclodextrin). The resulting mixture was heated to 55° C. overnight. The following day, the suspension was cooled to ambient temperature added dropwise to a vigorously stirring 500 mL Erlenmeyer flask filled with 300 mL of acetone to induce precipitation of the product. Stirring of the suspension was done at ambient temperature for 10 minutes and the fine precipitate (white flakes) were collected by centrifugation. The white precipitate was taken up in deionized water (50 mL) and the suspension was heated using a heat gun until the solid was fully solubilized. The solution was allowed to stand at ambient temperature for 2 hours, during which time a white, fine solid began to slowly precipitate. The suspension was centrifuged and the collected white solid (after carefully decanting the water layer) was washed with acetone (3×40 mL) and dried under vacuum for 4 hours. The process provides SuβN−1 (6) in pure form as a flaky, white solid (0.97 g, 82%). $^1$H NMR (D$_2$O, 600 MHz) δ 4.99 (d, J=3.6, 6H), 3.80 (t, J=9.6, 6H), 3.77 (t, J=9.6, 6H), 3.62 (t, J=6.0, 12H), 3.51 (dd, J=10.2, 3.6, 6H), 3.41 (t, J=9.6, 6H), 3.10 (d, J=12.0, 6H), 2.43 (app dd, J=13.8, 9.0, 6H), 2.72-2.68 (m, 12H); $^{13}$C NMR (D$_2$O, 150 MHz) δ 100.9, 83.6, 72.7, 71.7, 71.2, 60.4, 34.6, 33.2; LC-MS (TOF): [M+FA−H]$^-$, m/z 1599.3931 (1599.3905 calc.)

Preparation of SuβN (8)

Heptakis-6-deoxy-6-bromo-β-cyclodextrin 2 (1.0 g, 0.63 mmol) was made into a suspension with N-methyl-2-pyrrolidone (NMP, 20 mL) in a 100 mL round bottomed flask equipped with a stir bar. Upon gentle heating the cyclodextrin fully dissolved forming a light tan-colored solution. To this solution, cesium carbonate (2.1 g, 6.3 mmol, 10 equiv. to cyclodextrin) was added in small portions followed by the addition via syringe of 3-mercapto-1-propanol (0.54 mL, 0.58 g, 6.3 mmol, 10 equiv. to cyclodextrin). The resulting mixture was heated to 55° C. overnight. The following day, the suspension was cooled to ambient temperature added dropwise to a vigorously stirring 500 mL Erlenmeyer flask filled with 300 mL of acetone to induce precipitation of the product. Stirring of the suspension was done at ambient temperature for 10 minutes and the fine precipitate (white flakes) were collected by centrifugation. The white precipitate was taken up in deionized water (50 mL) and the suspension was heated using a heat gun until the solid was fully solubilized. The solution was allowed to stand at ambient temperature for 2 hours, during which time a fine, white solid began to slowly precipitate. The suspension was centrifuged and the collected white solid (after carefully decanting the water layer) was washed with acetone (3×40 mL) and dried under vacuum for 4 hours. The process provides the neutral, SuβN (8) in pure form as a white solid (0.88 g, 84%). $^1$H NMR (D$_2$O, 600 MHz) δ 5.07 (s, 6H), 3.88-3.83 (m, 12H), 3.63-3.60 (m, 18H), 3.48 (t, J=9.0, 6H), 3.19 (d, J=13.2, 6H), 2.72-2.68 (m, 12H), 1.80 (t, J=5.4, 12H; $^{13}$C NMR (D$_2$O, 150 MHz) δ 101.1, 84.0, 72.9, 71.8, 71.5, 60.4, 33.5, 31.7, 29.2; LC-MS (TOF): [M+FA−H]$^-$, m/z 1697.4975 (1697.5000 calc.)

Preparation of SuβN+1 (10)

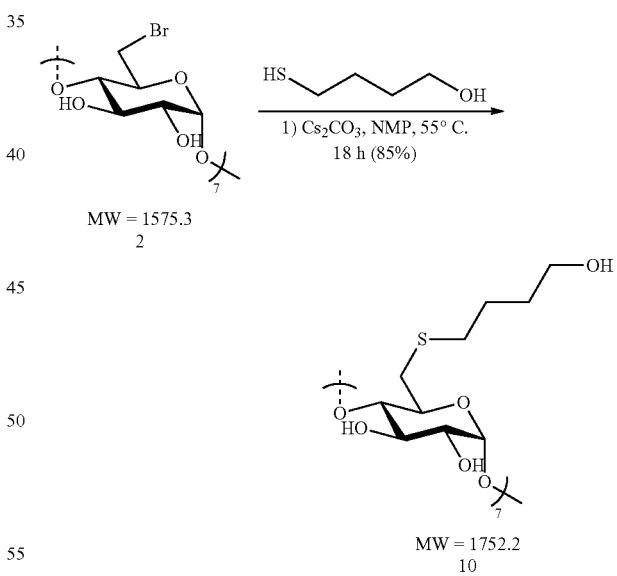

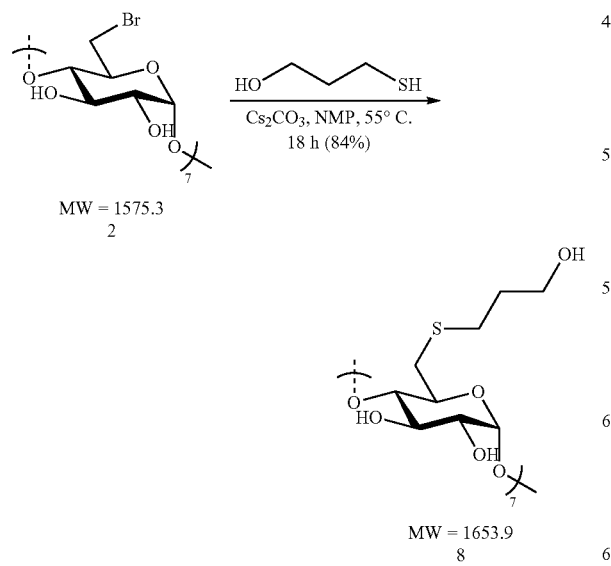

Heptakis-6-deoxy-6-bromo-β-cyclodextrin 2 (1.1 g, 0.7 mmol) was made into a suspension with N-methyl-2-pyrrolidone (NMP, 20 mL) in a 100 mL round bottomed flask equipped with a stir bar. Upon gentle heating the cyclodextrin fully dissolved forming a light tan-colored solution. To this solution, cesium carbonate (2.3 g, 7.0 mmol, 10 equiv. to cyclodextrin) was added in small portions followed by the addition via syringe of methyl 4-mercapto-1-butanol (0.72 mL, 0.74 g, 7.0 mmol, 10 equiv. to cyclodextrin). The resulting mixture was heated to 55° C. overnight. The following day, the suspension was cooled to ambient temperature added dropwise to a vigorously stirring 500 mL Erlenmeyer flask filled with 300 mL of acetone to induce precipitation of the product. Stirring of the suspension was done at ambient temperature for 10 minutes and the fine precipitate (white flakes) were collected by centrifugation. The white precipitate was taken up in deionized water (50 mL) and the suspension was heated using a heat gun until the solid was fully solubilized. The solution was allowed to stand at ambient temperature for 2 hours, during which time a fine, white solid began to slowly precipitate. The suspension was centrifuged and the collected white solid (after carefully decanting the water layer) was washed with acetone (3×40 mL) and dried under vacuum for 4 hours. The process provides SuβN+1 (10) in pure form as a white solid (1.04 g, 85%). $^1$H NMR (D$_2$O, 600 MHz) δ 5.05 (d, J=3.6, 6H), 3.86-3.81 (m, 12H), 3.61 (dd, J=9.6, 3.6, 6H), 3.55 (t, J=6.0, 12H), 3.46 (t, J=9.0, 6H), 3.20 (d, J=12.6, 6H), 2.86 (dd, J=13.8, 9.6, 6H), 2.72-2.64 (m, 12H), 1.64-1.59 (m, 24H); $^{13}$C NMR (D$_2$O, 150 MHz) δ 101.2, 84.2, 73.0, 71.9, 71.7, 61.3, 33.5, 32.7, 31.0, 25.8; LC-MS (TOF): [M+FA–H]$^-$, m/z 1795.6126 (1795.6069 calc.)

Example 2: Binding of CDs with Fentanyl Related Compounds

Equilibrium binding constants between the subetadex family and fentanyl HCl were determined using $^1$H NMR titration experiments. In order to derive the binding constant, the cyclodextrin concentration [H]T (in units of M) satisfied the inequality $[H]_T K<1$ (Shalley 2011), whenever possible. Initial studies required best-guess estimates of K since they were a priori unknown. Ultimately, this condition was satisfied for all compounds save for suβ+1, where the required concentration yielded an unacceptable signal-to-noise ratio. Use of this non-ideal concentration lead to a larger uncertainty in the derived binding constant (vide infra) (Thordarson 2011).

Each of the modified cyclodextrins was dissolved into D$_2$O to a total volume of 500 μL. 1 μL of acetonitrile was added as a chemical shift reference. Fentanyl HCl was then titrated into the solution. The total (bound to cyclodextrin+ free in solution) fentanyl HCl concentration $[G]_T$ (in units of M) was varied to cover the range of concentrations between $$\frac{(0.2[H]_T + 0.25)}{K} \text{ and } \frac{(0.8[H]_T + 4)}{K}$$

(Shalley 2011) for extraction of binding constants. At each titration point, the proton chemical shifts (referenced to acetonitrile at 2.01443 ppm) of the H1, H3, H5, and H6 protons on the CD were recorded; subtraction of the chemical shift obtained from the first data point, consisting of the cyclodextrin alone, yielded a difference between bound and free chemical shift $\Delta\delta_i$ for each of reporter proton i. The resultant curves of $\Delta\delta_i$ versus $[G]_T$ were then initially fit (Mathematica 10, Wolfram Research, Champaign, Ill.) using a non-linear least squares algorithm (Shalley 2011; Thordarson 2011; Mayer et al. 2016). As shown in Mayer et al., the binding constant K and a chemical shift sensitivity factor $\Delta\delta_{c,i}$ for each reporter proton are the fitting parameters (Mayer et al. 2016). Restricting K to a single value for each NMR titration curve yielded a global binding constant incorporating data from all reporter protons. All experiments were conducted in triplicate. Reported values of K for each compound are the average and standard deviation across the three experiments.

TABLE 2

NMR-derived binding affinities and energies from molecular dynamics simulations for CD:fentanyl complexes

| K (M$^{-1}$) | fentanyl | | acetylfentanyl | | thiofentanyl | | acetylchiofentanyl | |
| --- | --- | --- | --- | --- | --- | --- | --- | --- |
| | HCl | citrate | HCl | citrate | HCl | citrate | HCl | citrate |
| αCD | 151 (13) | — | 154 (29) | — | 145 (10) | — | 126 (20) | — |
| βCD | 279 (10) | 268 (19) | 161 (16) | 143 (15) | 235 (17) | 201 (16) | 152 (10) | 162 (11) |
| 2HP-βCD | 132 (25) | — | 64 (8) | — | 88 (9) | — | 104 (10) | — |
| 6amino-βCD | 174 (16) | — | 66 (8) | — | 177 (33) | — | 108 (28) | — |
| γCD | <30 | — | <30 | — | — | — | — | — |

$^a$Binding was shown to be independent of counteranion, so data for citrate salts are given only for βCD hosts. Values in parentheses are estimated errors (confidences) associated with the NLLS data regression.

Example 3: Binding of Thioether Modified CDs with Fentanyl (in the Form of a HCl Salt)

Equilibrium binding constants between the subetadex panel and fentanyl HCl were determined using $^1$H NMR titration experiments. Experiments were designed such that the CD concentration $[H]_T$ (in units of M) satisfied the inequality $[H]_T K<1$ whenever possible. (Shalley 2011). Initial studies required best-guess estimates of K since they were a priori unknown. The NMR chemical shifts of reporter protons on CD were monitored while the fentanyl titrant solution was added stepwise. Non-linear least squares fitting was performed assuming a 1:1 binding model for all proton titration curves simultaneously yielding a global binding affinity for each CD:fentanyl pair. (Mayer et al. 2016) Due to the limited aqueous solubilities of the neutral compounds 6, 8, and 10 (<1 mg mL$^{-1}$ in all cases), all titrations were conducted at $[H]_T<0.1$ mM. Results from this fitting procedure are given in the first data column of Table 3.

TABLE 3

NMR-derived binding affinities and energies from molecular dynamics simulations of thioether modified CDs with fentanyl

| | NMR simple | | | MD Results | |
| --- | --- | --- | --- | --- | --- |
| | 1:1 | NMR competitive 1:1 | | $<U + W>_{up}/$ | $<U + W>_{down}/$ |
| CDs | K/mM$^{-1}$ | K$_1$/mM$^{-1}$ | K$_2$/mM$^{-1}$ | kcal mol$^{-1}$ | kcal mol$^{-1}$ |
| suβ – 1 | 21.7 ± 7.0 | —[b] | —[b] | −27.7 ± 0.5 | −30.8 ± 1.4 |
| suβ – 0 | 30.1 ± 6.2 | 44 ± 22 | 2.1 ± 1.1 | −31.7 ± 0.6 | −30.8 ± 1.2 |
| suβ + 1 | —[a] | 67 ± 23 | 2.5 ± 0.5 | −38.6 ± 2.8 | −32.8 ± 0.6 |
| suβ – 1n | 2.7 ± 0.15 | —[b] | —[b] | −33.6 ± 1.4[c] | — |
| suβ – 0n | 1.6 ± 0.14 | —[b] | —[b] | −35.5 ± 1.2[c] | — |
| suβ + 1n | 0.2 ± 0.04 | —[b] | —[b] | −37.6 ± 1.8[c] | — |
| sugammadex | 7.9 ± 1.9 | —[d] | —[d] | —[d] | —[d] |

[a] 1:1 model did not hold.
[b] More complex model not necessary to fit titration data.
[c] Only "up" orientation of fentanyl simulated.
[d] A multi-conformation analysis was not necessary to describe the NMR titration data.

FIG. 1 shows NMR-determined binding affinities for 1:1 host:guest complexes versus enthalpic energies determined from simulation for the dominant conformer of fentanyl bound to CDs 5-10 (MD binding energies), and to unmodified α- and β-CDs as provided in Table 2 of Example 2. The solid line showed a linear fit taking into account of measurement uncertainty. The MD binding energies obtained have values provided in the final two columns of Table 3. For the anionic suβ–1, suβ–0, and suβ+1 (5, 7, and 9), NMR results correlated well with behavior predicted by MD.

Binding affinity increased as did binding energy of the modified anionic βCDs as the size of the modification group increased. See, e.g., binding energy increased from suβ–1n to supβ+1n. Such increased affinity with increased modification group size may be due to the enhanced van der Waals interactions afforded by the elongated anionic thioether modification group (also referred to as arms of the modified CDs). Thus, CDs modified with anionic thioether groups longer than those of suβ+2 (e.g., n is 5, 6, 7, 8, 9, or 10 for compounds of Formula I and II) may display similar binding affinities for fentanyl related compounds.

Similar to their anionic counterparts, initial MD simulations suggested enhanced binding affinities with increased arm length for the neutral thioether modified CDs. NMR data, however, showed a dramatic decrease in binding affinity, one that weakened with increased arm length (see Table 3, FIG. 1). NMR structural data from ROESY experiments showed interaction between interior CD protons and those from the thioalkyl alcohol arms. Additional MD simulations of these lone hosts (modified neutral CDs) in solution confirmed this behavior. Without being bound by any theory, the neutral hydrophobic arms may interact with their own hydrophobic CD interior, therefore blocking fentanyl related compounds from binding to these CDs.

Without being bound by any theory, for the CDs modified with anionic arms as disclosed herein, the anionic modifications (e.g., the carboxylate arms) may improve the aqueous solubility of the modified CDs and keep the anionic thioether modified supβdex accessible to binding by the target compounds (e.g., fentanyl related compounds) through electrostatic repulsion among the anionic arms. For example, MD suggests that there was little interaction between the carboxylate terminuses and the fentanyl molecule, as the charged groups oriented into their aqueous surrounding. Without being bound by any theory, the additional methylene groups of the arms elongated the CD hydrophobic cavity and may contribute to the increase in observed K values through additional van der Waals attraction with its fentanyl guest.

Figure 2A:
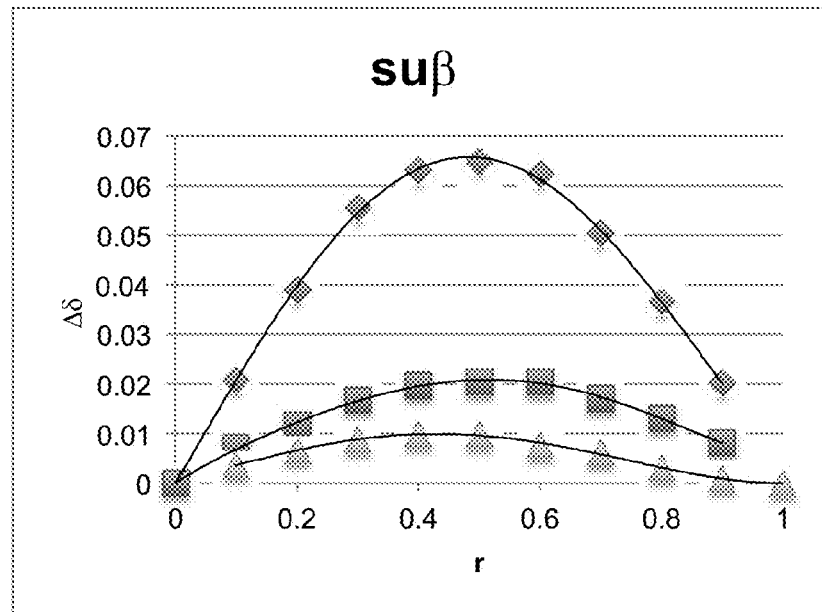
FIG. 2a: Job plots of sup complex with fentanyl HCl: diamonds:H5 protons, squares:H2 protons, and triangles: amide-end aromatic protons.
Figure 2B:
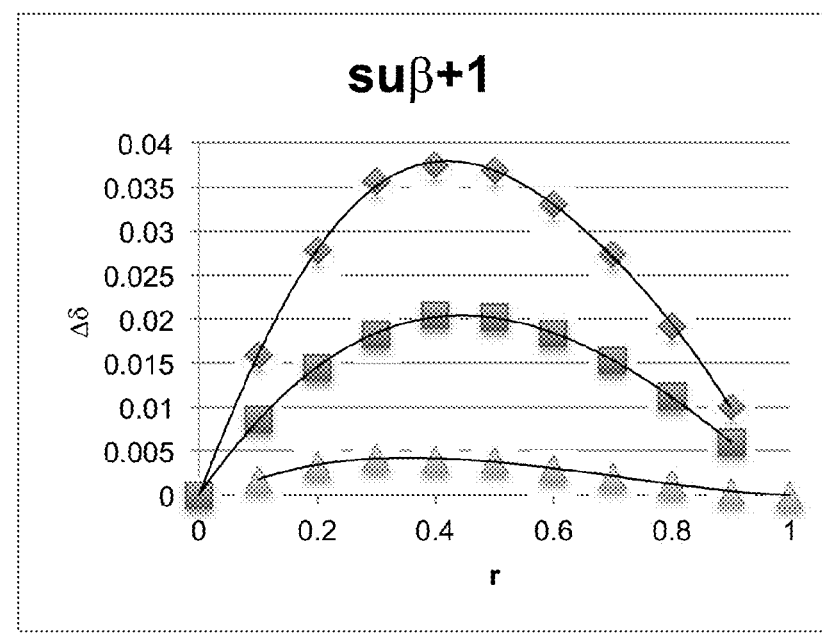
FIG. 2b: Job plots of suβ+1 complex with fentanyl HCl:diamonds:H5 protons, squares:H2 protons, and triangles:amide-end aromatic protons.

The results presented supra represented a simplified view of structural details of the subetadex:fentanyl complexes. NMR data in the form of Job plots (FIGS. 2a and 2b), which were used to determine host:guest stoichiometries, revealed complex binding behavior initially thought to originate from a 1:2 or 2:1 host:guest complex. MD simulations, however, showed the modified βCDs could not accommodate a second fentanyl molecule with any appreciable stability.

Figure 3C:
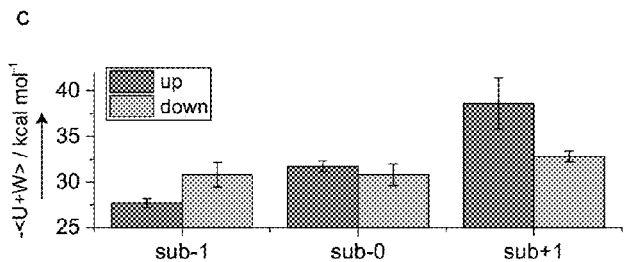

Simulations involving two distinct fentanyl orientations within the charged βCDs (suβ–1, suβ–0, and suβ+1), however, were shown to be favorable with relatively small differences in energies between the two possible conformations (0.8 to 5.8 kcal mol$^{-1}$, FIG. 3c). In the case of suβ–1, the orientation with the amide half of fentanyl pointed "down" toward the anionic chain ends was energetically favored over fentanyl in the opposite direction (see FIG. 3a). For suβ+1, the reversed configuration was favored with the amide half pointed "up" toward the unmodified secondary rim of the modified βCDs (see FIG. 3b). For suβ–0, the two conformations were roughly equally favorable.

Figure 4A:
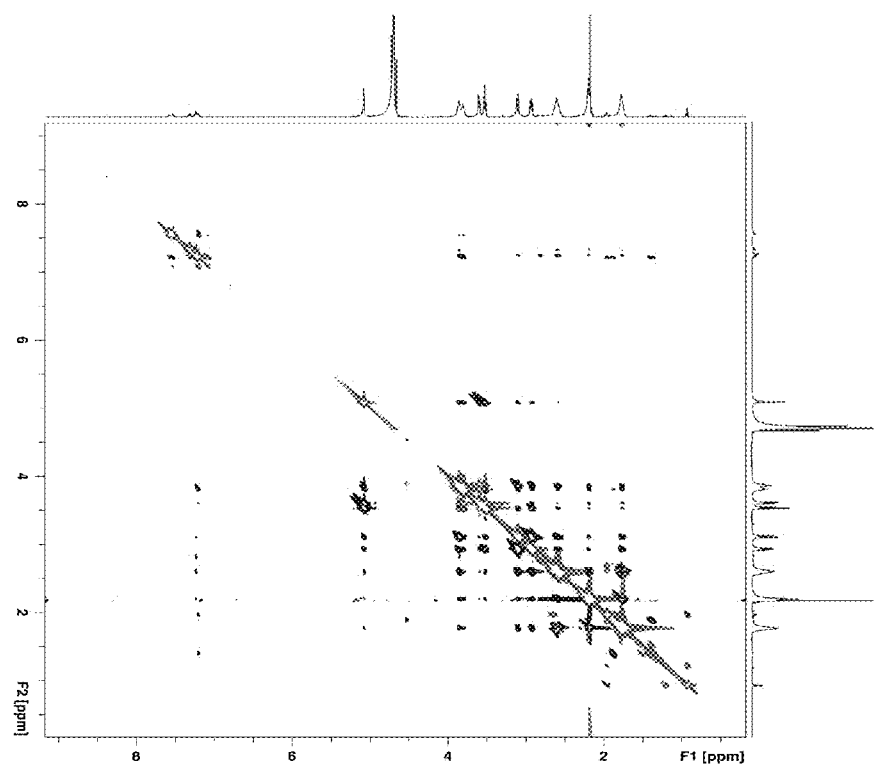
FIG. 4a: An exemplary two-dimensional ROESY spectrum of a 1:3.7 fentanyl HCl/suβ+1 mixture.
Figure 4B:
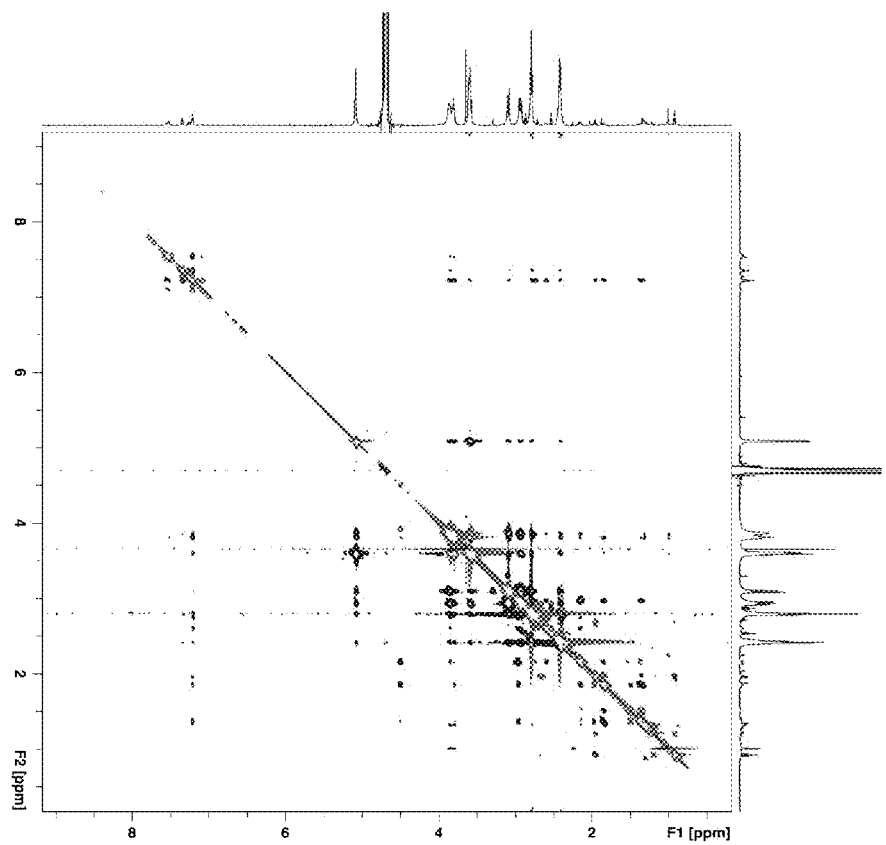
FIG. 4b: An exemplary two-dimensional ROESY spectrum of a 1:3.7 fentanyl HCl/suβ mixture.

This behavior was consistent with ROESY NMR experiments. For example, FIGS. 4a and 4b give the two-dimensional ROESY spectrum of a 1:3.7 fentanyl HCl/suβ+1 mixture and a 1:3.7 fentanyl HCl/suβ mixture, respectively. The correlations between methylene protons on the anionic arm and aromatic protons on the amide nitrogen-bound phenyl ring were absent. Rather, only correlations between these methylenes and the phenethyl aromatic protons were found. This indicates the overwhelming majority of fentanyl bound in the "down" orientation. ROESY data for a suβ–1/fentanyl mixture showed similar agreement to MD data, especially a strong correlation between amide phenyl protons and interior CD protons towards its unmodified, secondary rim. This correlation provided evidence of the existence of the "up" orientation. In all cases, all Job Plot data suggested a multi-conformation binding system regardless of the presence or lack of the corresponding ROESY correlations. These experiments were much more sensitive at detecting multi-conformation binding modes, as they cover a substantially wider relative concentration range (i.e. [H]$_0$/[G]$_0$ ratio) than titration experiments. Confident values of highly correlated fitting parameters may be extracted from simultaneously fitting Job Plot and titration data.

The likely coexistence of the two conformations in fentanyl HCl:suβ−0 and fentanyl HCl:suβ+1 complexes suggests that the 1:1 binding fitting procedure previously discussed may be too simplistic a model. A "multi-conformation" model was developed to explicitly consider the existence of two distinct guest molecule orientations on the chemical shift titration data. Results from this fitting procedure are provided in the data column of Table 3 under "NMR competitive 1:1." This "multi-conformation" model yielded two sets of binding constants, one for each of the orientations. One, larger set of constants were statistically similar to those derived from the 1:1 model for suβ−0. Secondary binding constants indicative of the weaker complex were also extracted, but it was not possible to unambiguously assign affinities to particular conformations with titration data alone. The apparent agreement of NMR ROESY data with the MD results, however, seems to suggest that the preferred conformation obtained from NMR data agreed with those with the highest computed energies (i.e. most enthalpically favorable) as given in FIG. 3. We plotted binding constants obtained for the more robust 1:1 model in FIG. 1 (with suβ+1 being the exception).

In summary, predictions of the fentanyl-subetadex binding constants from MD simulations were generally in good agreement with data obtained from NMR experiments: binding strength increased as the length of the modified arm increased for the anionic thioether modified β-CDs. For the electrically neutral thioether modified β-CDs, however, experimentally determined binding affinities decreased with arm length. The anionic thioether modified β-CDs Suβ−1, Suβ−0, and Suβ+1 showed an increasing trend in binding constant, with a maximum K=66,500 M$^{-1}$ for Suβ+1. These are by far the largest equilibrium binding constants reported for fentanyl-cyclodextrin complexes. Thus, these thioether modified β-CDs could find use in medical countermeasures, biosensing, and environmental pollutant remediation.

References listed below are herein incorporated by reference in their entireties:

Abramowitz, A. Elementary Analytical Methods. In *Handbook of Mathematical Functions: with Formulas, Graphs, and Mathematical Tables*; Abramowitz, M., Stegun, I. A.; Dover Publications, Inc.: New York, N.Y., 1965.

Baer, H. H.; Vargas Berenguel, A.; Shu, Y. Y.; Defaye, J.; Gadelle, A.; Santoyo Gonzalez, F., 1992. *Carbohydr. Res.* 228, 307-14.

Berendsen, H. J. C.; Postma, J. P. M.; van Gunsteren, W. F.; DiNola, A.; Haak, J. R., 1984. Molecular-Dynamics with Coupling to an External Bath. *J. Chem. Phys.* 81, 3684-90.

Case, D. A.; Cheatham, T. E. 3rd; Darden, T.; Gohlke, H.; Luo, R.; Merz K. M. Jr.; Onufriev, A.; Simmerling, C.; Wang, B.; Woods, R., 2005. The Amber Biomolecular Simulation Programs. *J. Comput. Chem.* 26, 1668-88.

Cézard, C.; Trivelli, S.; Aubry, F.; Djedaïni-Pilard, F.; Dupreadeu, F. Y., 2011. Molecular Dynamics Studies of Native and Substituted Cyclodextrins in Different Media: 1. Charge Derivation and Force Field Performances. *Phys. Chem. Chem. Phys.* 13, 15103-21.

Cooper, A.; Nutley, M.; MacLean, E. J.; Cameron, K.; Fielding, L.; Mestres, J.; Palin, R. 2005. *Mutual Induced Fit in Cyclodextrin-Rocuronium Complexes*. Org. Biomol. Chem. 3, 1863-1971.

Cameron, K. S., Fletcher, D., and Fielding, L, 2002. *An NMR Study of Cyclodextrin Complexes of the Steroidal Neuromuscular Blocker Drug Rocuronium Bromide*. Magn. Reson. Chem. 40, 251-260.

Cameron, K. S.; and Fielding, L. 2002. *NMR Diffusion Coefficient Study of Steroid-Cyclodextrin Inclusion Complexes*. Magn. Reson. Chem. 40, S106-S109.

Højsted, J. and Sjøgren, P., 2007. *Addiction to Opioids in Chronic Pain Patients: a Literature Review*, Eur. J. Pain, 11, 490-518.

Darden, T.; York, D.; Pedersen, L., 1993. Particle mesh Ewald: An N log(N) Method for Ewald Sums in Large Systems. *J. Chem. Phys.* 98, 10089-92.

Jakalian, A.; Bush, B. L.; Jack, D. B.; Bayly, C. I. Fast, 2000. Deficient Generation of High-Quality Atomic Charges. AM1-BCC Model: I. Method. *J. Comput. Chem.* 21, 132-46.

Jorgensen, W. L.; Chandrasekhar, J.; Madura, J. D.; Impey, R. W.; Klein, M. L., 1983. Comparison of simple potential functions for simulating liquid water. *J. Chem. Phys.* 79, 926.

Kollman, P. A.; Massova, I.; Reyes, C.; Kuhn, B.; Huo, S.; Chong, L.; Lee, M.; Lee, T.; Duan, Y.; Wang, W.; Donini, O.; Cieplak, P.; Srinivasen, J.; Case, D. A.; Cheatham, T. E. III., 2000. Calculating Structures and Free Energies of Complex Molecules: Combining Molecular Mechanics and Continuum Models. *Acc. Chem. Res.* 33, 889-97.

Mayer, B. P., Kennedy, D. J., Lau, E. Y., and Valdez, C. A., 2016. *Solution-State Structure and Affinities of Cyclodextrin:Fentanyl Complexes by Nuclear Magnetic Resonance Spectroscopy and Molecular Dynamics Simulation*. J. Phys. Chem. B, 120, 2423-33.

Miller, B. R. III.; McGee, T. D. Jr.; Swails, J. M.; Homeyer, N.; Gohlke, H.; Roitberg, A. E., 2012. MMPBSA.py: An Efficient Program for End-State Free Energy Calculations. *J. Chem. Theory Comput.* 8, 3314-21.

Onufriev, A.; Bashford, D.; Case, D. A., 2004. Exploring Protein Native States and Large-Scale Conformational Changes with a Modified Generalized Born Model. *Proteins. Struc., Func., Bioinf* 55, 383-94.

Peng, P. W. H., and Sandler, A. N., 1999. *A Review of the Use of Fentanyl Analgesia in the Management of Acute Pain in Adults*, Anesthesiology, 90, 576-599.

Pettersen, E. F.; Goddard, T. D.; Huang, C. C.; Greenblatt, D. M.; Meng, E. C.; Ferrin, T. E., 2004. UCSF Chimera—a Visualization System for Exploratory Research and Analysis. *J. Comput. Chem.* 25, 1605-12.

Ryckaert, J.-P.; Cicotti, G.; Berendsen, H. J. C., 1977. Numerical Integration of the Cartesian Equations of Motion of a System with Constrains: Molecular Dynamics of n-Alkanes. *J. Comput. Phys.* 23, 327-341.

Sehgal, N., Manchikanti, L., and Smith, H. S. 2012. *Prescription Opioid Abuse in Chronic Pain: a Review of Opioid Abuse Predictors and Strategies to Curb Opioid Abuse*, Pain Physician, 15, ES67-ES92.

Shalley, C. A., 2011. *Analytical Methods in Supramolecular Chemistry, Second, Completely Revised and Enlarged Edition*, Wiley-VCH, Weinheim, Pages 27-66.

Thordarson, P., 2011. *Determining Association Constants from Titration Experiments in Supramolecular Chemistry*, Chem. Soc. Rev. 40, 1305-23.

Wang, J.; Wolf, R. M.; Caldwell, J. W.; Kollman, P. A.; Case, D. A., 2004. Development and Testing of a General Amber Force Field. *J. Comput. Chem.* 25, 1157-74.

What is claimed is:

1. A compound of Formula I:

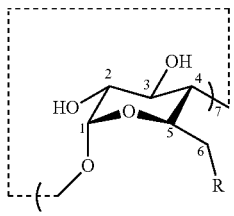

Formula I including salts and pharmaceutically acceptable salts thereof, wherein:

R is $-S-(CH_2)_n-COOH$ or $-S-(CH_2)_{n+1}-OH$; and n is 8, 9, or 10.

2. The compound of claim 1, wherein R is $-S-(CH_2)_n-COOH$, and the salt or pharmaceutically acceptable salt is potassium salt, and/or sodium salt.

3. A composition comprising the compound of claim 1 and optionally a carrier.

4. A pharmaceutical composition comprising the compound of claim 1 and optionally a pharmaceutically acceptable carrier.

5. A method of preparing the compound of claim 1 comprising:

a) a coupling step comprising reacting a thiol R'—H and a per-7-Br-βCD to provide a coupling β-CD product:

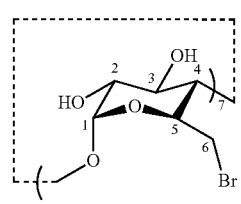

Per-7-Br-βCD

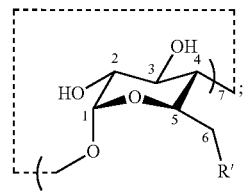

Coupling β-CD product wherein R' $-S-(CH_2)_n-COOH$.

* * * * *